US010571456B2

(12) United States Patent
Katsumoto et al.

(10) Patent No.: US 10,571,456 B2
(45) Date of Patent: Feb. 25, 2020

(54) ELECTRICAL MEASURING CARTRIDGE, ELECTRICAL MEASURING APPARATUS FOR BIOLOGICAL SAMPLE, ELECTRICAL MEASURING SYSTEM FOR BIOLOGICAL SAMPLE, AND ELECTRICAL MEASURING METHOD FOR BIOLOGICAL SAMPLE

(71) Applicant: SONY CORPORATION, Tokyo (JP)

(72) Inventors: Yoichi Katsumoto, Tokyo (JP); Marcaurele Brun, Tokyo (JP); Yoshihito Hayashi, Chiba (JP)

(73) Assignee: SONY CORPORATION, Tokyo (JP)

( * ) Notice: Subject to any disclaimer, the term of this patent is extended or adjusted under 35 U.S.C. 154(b) by 309 days.

(21) Appl. No.: 15/323,745

(22) PCT Filed: Jun. 2, 2015

(86) PCT No.: PCT/JP2015/065875
§ 371 (c)(1),
(2) Date: Jan. 4, 2017

(87) PCT Pub. No.: WO2016/013300
PCT Pub. Date: Jan. 28, 2016

(65) Prior Publication Data
US 2017/0160261 A1    Jun. 8, 2017

(30) Foreign Application Priority Data

Jul. 24, 2014    (JP) ................................. 2014-150782

(51) Int. Cl.
| | | |
|---|---|---|
| G01N 33/49 | (2006.01) | |
| G01N 27/06 | (2006.01) | |
| C12Q 1/00 | (2006.01) | |

(52) U.S. Cl.
CPC ............. *G01N 33/49* (2013.01); *G01N 27/06* (2013.01)

(58) Field of Classification Search
CPC ........ G01N 1/00; G01N 2201/00; C12Q 1/00; C12Q 2304/00
See application file for complete search history.

(56) References Cited

U.S. PATENT DOCUMENTS

| | | | | |
|---|---|---|---|---|
| 5,583,432 A | * | 12/1996 | Barnes | ................... G01N 15/05 324/204 |
| 6,150,174 A | * | 11/2000 | Sin | ...................... G01N 33/4905 422/73 |

(Continued)

FOREIGN PATENT DOCUMENTS

| | | |
|---|---|---|
| JP | 2009-042141 A | 2/2009 |
| JP | 2010-181400 A | 8/2010 |

(Continued)

*Primary Examiner* — Huy Q Phan
*Assistant Examiner* — Temilade S Rhodes-Vivour
(74) *Attorney, Agent, or Firm* — Chip Law Group

(57) ABSTRACT

Provided is an electrical measuring cartridge including at least: a biological sample holding section that accommodates a liquid biological sample containing a sedimenting component; a measuring electrode unit that is fixed to the biological sample holding section and composed of a pair of electrodes for electrically measuring a state of the biological sample; and a sedimentation measuring electrode unit that is fixed to a position at a different height from the measuring electrode unit of the biological sample holding section and composed of a pair of electrodes for electrically measuring a degree of sedimentation of the sedimenting component.

18 Claims, 10 Drawing Sheets

(56) References Cited

U.S. PATENT DOCUMENTS

| | | | |
|---|---|---|---|
| 7,021,122 B1* | 4/2006 | Rosemberg | G01N 11/04 |
| | | | 73/304 C |
| 7,648,836 B1* | 1/2010 | Scott | G01N 22/00 |
| | | | 422/416 |
| 2002/0132351 A1* | 9/2002 | Szecsody | B09C 1/00 |
| | | | 436/25 |
| 2006/0252054 A1* | 11/2006 | Lin | A61M 1/36 |
| | | | 435/6.11 |
| 2009/0314066 A1* | 12/2009 | Nieuwenhuis | G01N 15/0656 |
| | | | 73/61.71 |

FOREIGN PATENT DOCUMENTS

| | | |
|---|---|---|
| JP | 2012-052906 A | 3/2012 |
| JP | 2014-115256 A | 6/2014 |

* cited by examiner

ELECTRICAL MEASURING CARTRIDGE, ELECTRICAL MEASURING APPARATUS FOR BIOLOGICAL SAMPLE, ELECTRICAL MEASURING SYSTEM FOR BIOLOGICAL SAMPLE, AND ELECTRICAL MEASURING METHOD FOR BIOLOGICAL SAMPLE

CROSS REFERENCE TO RELATED APPLICATIONS

This application is a U.S. National Phase of International Patent Application No. PCT/JP2015/065875 filed on Jun. 2, 2015, which claims priority benefit of Japanese Patent Application No. JP 2014-150782 filed in the Japan Patent Office on Jul. 24, 2014. Each of the above-referenced applications is hereby incorporated herein by reference in its entirety.

TECHNICAL FIELD

The present technology relates to an electrical measuring cartridge for measuring an electrical property of a liquid biological sample containing sedimenting components. More specifically, the present technology relates to an electrical measuring cartridge for a liquid biological sample containing sedimenting components having a structure that can improve the measurement accuracy, an electrical measuring apparatus for a biological sample using the electrical measuring cartridge, an electrical measuring system for a biological sample, and an electrical measuring method for a biological sample.

BACKGROUND ART

Measurement of electrical properties of a biological sample, determination of physical properties of the biological sample from the measurement result, and discrimination of a kind of cell or the like included in the biological sample, and so on, are performed (for example, see Japanese Patent Application Laid-open No. 2009-042141). The measured electrical properties may be complex permittivity or frequency dispersion (a dielectric spectrum) thereof. The complex permittivity or the frequency dispersion is generally calculated by measuring a complex capacitance and complex impedance between electrodes using a solution retainer or the like including the electrodes configured to apply a voltage to a solution.

In addition, for example, in Japanese Patent Application Laid-open No. 2010-181400, a technology of obtaining information related to blood coagulation from permittivity of blood is disclosed, and "a blood coagulation system analysis device including a pair of electrodes, an application unit configured to apply an alternating current voltage to the pair of electrodes at predetermined time intervals, a measurement unit configured to measure the permittivity of the blood disposed between the pair of electrodes, and an analysis unit configured to analyze a level of function of the blood coagulation system using the permittivity of the blood measured at the time intervals after an action of the anticoagulant agent functioned in the blood is released" is disclosed.

When the electrical properties of the biological sample are measured, as a container configured to accommodate the biological sample, for example, Japanese Patent Application Laid-open No. 2012-052906 discloses a sample cartridge having a cylindrical body made of an insulating material, configured to hold the biological sample in a region including surfaces of electrodes inserted into an inner hole from both of end openings and a surface of the inner hole, and in which a constriction section disposed between the two opposite electrodes and formed by constricting the inner hole is installed at that region, measuring electrical properties of a biological sample.

Here, thus far, there has been known a problem that, when measuring an electrical property of a liquid biological sample containing sedimenting components, the sedimentation over time of sedimenting components influences the measurement result, and consequently the measurement accuracy is reduced.

For example, in the case where blood is selected as the biological sample and measurement is performed using the sample cartridge disclosed in Patent Literature 3, it is difficult to isolate the direct influence of the aggregation and coagulation process of blood and the influence of the change in blood sedimentation rate occurring in association with this. This is because the sample cartridge includes only a pair of electrodes for blood coagulation measurement and there is, depending on the disease, a strong correlation between blood coagulation and blood sedimentation rate, and therefore it is very difficult to assess whether the obtained measurement result reflects the degree of blood coagulation or reflects the sedimentation rate.

Further, also in the case where blood is selected as the biological sample and measurement is performed using a blood sedimentation meter, although the state of aggregation and coagulation of blood can be estimated from the change in blood sedimentation rate, only qualitative information is obtained because the accuracy is low because the estimation is an estimation dependent on a single model such as the Stokes equation or an empirical formula.

CITATION LIST

Patent Literature

Patent Literature 1: JP 2009-042141A
Patent Literature 2: JP 2010-181400A
Patent Literature 3: JP 2012-052906A

DISCLOSURE OF INVENTION

Technical Problem

As described above, in the conventional technology, it has been difficult to, when measuring an electrical property of a liquid biological sample containing sedimenting components, exclude the influence due to the sedimentation over time of sedimenting components on the measurement result.

Thus, a main object of the present technology is to provide an electrical measuring cartridge for a liquid biological sample containing sedimenting components having a structure that can improve the measurement accuracy.

Solution to Problem

In view of the issue mentioned above, the inventors of the present application conducted extensive studies on the structure of the cartridge used when measuring electrical properties, and successfully improved the measurement accuracy by providing a measuring electrode unit for measuring the state of the biological sample and a sedimentation measuring electrode unit that measures the degree of sedimentation of sedimenting components and fixing these electrode units to positions at different heights; and thus completed the present technology.

That is, the present technology first provides an electrical measuring cartridge including at least:

a biological sample holding section that accommodates a liquid biological sample containing a sedimenting component;

a measuring electrode unit that is fixed to the biological sample holding section and composed of a pair of electrodes for electrically measuring a state of the biological sample; and a sedimentation measuring electrode unit that is fixed to a position at a different height from the measuring electrode unit of the biological sample holding section and composed of a pair of electrodes for electrically measuring a degree of sedimentation of the sedimenting component.

According to the present technology, the measuring electrode unit and the sedimentation measuring electrode unit may be fixed apart from each other to such a degree that mutual lines of electric force do not interfere with each other.

In addition, the sedimentation measuring electrode unit may be fixed to a position lower than the measuring electrode unit of the biological sample holding section.

In addition, the sedimentation measuring electrode unit may be located on a lower side of a position where a cumulative deposition fraction from a portion that forms a bottom during measurement of the biological sample holding section is not less than a volume fraction of the sedimenting component.

In addition, the measuring electrode unit may be located on an upper side of a position where a cumulative deposition fraction from a portion that forms a bottom during measurement of the biological sample holding section is not less than a volume fraction of the sedimenting component.

In the present technology, although material of the biological sample holding section is not specifically limited, the biological sample holding section may be made of resin.

In addition, in the present technology, although the resin is not specifically limited, the resin may be one or more kinds of resin selected from polypropylene, polystyrene, acryl, and polysulfone.

In the present technology, although the biological sample is not specifically limited, the biological sample may be a blood sample.

In addition, the electrical measuring cartridge may be used for measurement of a state of blood coagulation.

The electrical measuring cartridge may be used as a part of an electrical measuring apparatus for a biological sample appropriately.

Specifically, there is provided an electrical measuring apparatus for a biological sample, the electrical measuring apparatus including at least:

a cartridge holding section that holds an electrical measuring cartridge including at least a biological sample holding section that accommodates a liquid biological sample containing a sedimenting component, a measuring electrode unit that is fixed to the biological sample holding section and composed of a pair of electrodes for electrically measuring a state of the biological sample, and a sedimentation measuring electrode unit that is fixed to a position at a different height from the measuring electrode unit of the biological sample holding section and composed of a pair of electrodes for electrically measuring a degree of sedimentation of the sedimenting component;

a first application unit that applies a voltage to the measuring electrode unit;

a second application unit that applies a voltage to the sedimentation measuring electrode unit;

a first measurement unit that measures an electrical property obtained from the measuring electrode unit; and a second measurement unit that measures an electrical property obtained from the sedimentation measuring electrode unit.

The electrical measuring apparatus for a biological sample may include a correction section that corrects a measurement result obtained from the first measurement unit using a measurement result obtained from the second measurement unit.

In addition, the electrical measuring apparatus for a biological sample may include a result sorting section that sorts a measurement result obtained from the first measurement unit using a measurement result obtained from the second measurement unit.

In addition, measurement in the first measurement unit and measurement in the second measurement unit may be performed at different timings.

In addition, measurement in the first measurement unit and measurement in the second measurement unit may be performed with different frequencies.

The electrical measuring cartridge may also be used as a part of an electrical measuring system for a biological sample appropriately.

Specifically, there is provided an electrical measuring system for a biological sample, the electrical measuring system including at least:

an electrical measuring apparatus for a biological sample, including at least a cartridge holding section for holding an electrical measuring cartridge, including at least a biological sample holding section that accommodates a liquid biological sample containing a sedimenting component, a measuring electrode unit that is fixed to the biological sample holding section and composed of a pair of electrodes for electrically measuring a state of the biological sample, and a sedimentation measuring electrode unit that is fixed to a position at a different height from the measuring electrode unit of the biological sample holding section and composed of a pair of electrodes for electrically measuring a degree of sedimentation of the sedimenting component, a first application unit that applies a voltage to the measuring electrode unit, a second application unit that applies a voltage to the sedimentation measuring electrode unit, a first measurement unit that measures an electrical property obtained from the measuring electrode unit, and a second measurement unit that measures an electrical property obtained from the sedimentation measuring electrode unit; and an analysis device that includes at least a correction section that corrects a measurement result obtained from the first measurement unit using a measurement result obtained from the second measurement unit.

In addition, in the electrical measuring system for a biological sample according to the present technology, the electrical measuring apparatus for a biological sample and the analysis device may be connected via a network.

Also, the electrical measuring cartridge according to an embodiment of the present technology may also be preferably used in an electrical measuring method for a biological sample of measuring electrical properties of a biological sample.

Specifically, there is provided an electrical measuring method for a biological sample, the electrical measuring method including:

measuring an electrical property of the biological sample using an electrical measuring cartridge including at least a biological sample holding section that accommodates a liquid biological sample containing a sedimenting component, a measuring electrode unit that is fixed to the biological sample holding section and composed of a pair of electrodes for electrically measuring a state of the biological sample, and a sedimentation measuring electrode unit that is fixed to a position at a different height from the measuring electrode unit of the biological sample holding section and composed of a pair of electrodes for electrically measuring a degree of sedimentation of the sedimenting component.

The electrical measuring method for a biological sample according to the present technology may additionally include at least:

a first application step of applying a voltage to the measuring electrode unit;

a second application step of applying a voltage to the sedimentation measuring electrode unit;

a first measurement step of measuring an electrical property obtained from the measuring electrode unit; and a second measurement step of measuring an electrical property obtained from the sedimentation measuring electrode unit.

Advantageous Effects of Invention

In an electrical measuring cartridge according to the present technology, a measuring electrode unit for measuring the state of the biological sample and a sedimentation measuring electrode unit that measures the degree of sedimentation of sedimenting components are provided, and these electrode units are fixed to positions at different heights; therefore, the influence due to the sedimentation of sedimenting components on the measurement result can be excluded, and the measurement accuracy can be improved. It is noted that the effects described herein are not necessarily limited, and any one of the effects described in the present technology may be exerted.

MODE(S) FOR CARRYING OUT THE INVENTION

Figure 1:
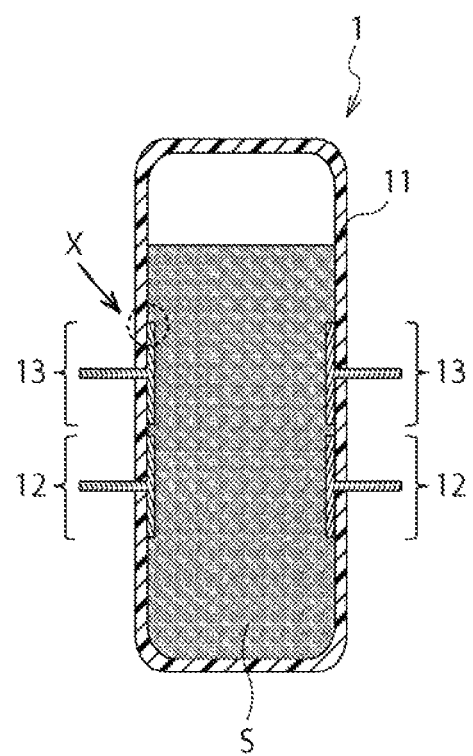
FIG. 1 is a schematic end view schematically showing a first embodiment of an electrical measuring cartridge 1 according to the present technology.

It is noted that embodiments described below are examples of a representative embodiment of the present technology, and do not cause the scope of the present technology to be narrowly interpreted. It is noted that description will be provided in the following order.
1. Electrical measuring cartridge 1
(1) Biological sample holding section 11
(2) Measuring electrode unit 12
(3) Sedimentation measuring electrode unit 13
First Embodiment
Second Embodiment
Third Embodiment
Fourth Embodiment
(4) Liquid biological sample S containing sedimenting components
(5) Other matters
2. Electrical measuring apparatus 10 for biological sample
(1) Cartridge holding section 2
(2) First application unit 31
(3) Second application unit 32
(4) First measurement unit 41
(5) Second measurement unit 42
(6) Correction section 5
(7) Result sorting section 6
(8) Other matters
3. Electrical measuring system 20 for biological sample
(1) Analysis device 201
(2) Server 202
(3) Display section 203
(4) User interface 204
4. Electrical measuring kit K for biological sample
(1) Biological sample introducing member 8
5. Electrical measuring method for biological sample
1. Electrical Measuring Cartridge 1

FIG. 1 is a schematic end view schematically showing a first embodiment of an electrical measuring cartridge 1 according to the present technology. The electrical measuring cartridge 1 according to the present technology is a cartridge used to, when measuring an electrical property of a liquid biological sample S containing sedimenting components, hold the biological sample S. The electrical measuring cartridge 1 according to the present technology roughly includes at least a biological sample holding section 11, a measuring electrode unit 12, and a sedimentation measuring electrode unit 13. Each part will now be described in detail. Although the biological sample S is shown in the drawing for convenience of description, the biological sample S is not included in the electrical measuring cartridge 1 according to the present technology.

(1) Biological Sample Holding Section 11

In the electrical measuring cartridge 1 according to the present technology, the biological sample holding section 11 is a part used to accommodate the liquid biological sample S containing sedimenting components that is the measurement target.

In the electrical measuring cartridge 1 according to the embodiment of the present technology, the form of the biological sample holding section 11 is not particularly limited, and can be freely designed depending on the type of the biological sample S, the measurement method, the electrical measuring apparatus to be used, and the like. Examples of the form may include a cylindrical body, a polygonal barrel having a polygonal cross section (triangle, square, or more), a circular cone, a polygonal cone having a polygonal cross section (triangle, square, or more), and one or a combination of two or more thereof.

In the present technology, for the biological sample holding section 11, it is preferable to select a form in which at least the portions where the measuring electrode unit 12 and the sedimentation measuring electrode unit 13 described later are disposed are in a planar shape. The reason will now be described in detail.

In general, the electrode used in electrical measurement is usually in a planar shape or a plate-like shape. When a circular cylindrical shape is selected in the biological sample holding section 11, the measuring electrode unit 12 and the sedimentation measuring electrode unit 13 in a planar shape or a plate-like shape are attached to a curved portion, and therefore the manufacturing process is very complicated. Furthermore, when the measuring electrode unit 12 and the sedimentation measuring electrode unit 13 in a planar shape or a plate-like shape are attached to a curved portion of the biological sample holding section 11, it is highly likely that a level difference will occur in the connection portions between the biological sample holding section 11, and the measuring electrode unit 12 and the sedimentation measuring electrode unit 13, and the measurement accuracy in electrical measurement may be reduced. Therefore, in the biological sample holding section 11, by selecting a form in which at least the portions where the measuring electrode unit 12 and the sedimentation measuring electrode unit 13 are disposed are in a planar shape, it becomes possible to simplify the manufacturing process of the electrical measuring cartridge 1 and improve the measurement accuracy.

According to an embodiment of the present technology, in a state in which the biological sample S is held in the biological sample holding section 11, various kinds of electrical properties measurement is performed. For this reason, the biological sample holding section 11 may be configured to be sealable in a state in which the biological sample S is held. However, a time to perform various kinds of electrical properties measurement of the biological sample S may be delayed, and the section may not be configured to be sealable as long as the measurement is not influenced.

An introducing or encapsulating method of the biological sample S into the biological sample holding section 11 is not particularly limited, and the biological sample S can be introduced or encapsulated in an optional method depending on the form of the biological sample holding section 11. An example thereof may include, although not illustrated in the drawings, a method of introducing the biological sample S into the biological sample holding section 11 using a pipette; and a method of sticking and inserting an injection needle from an outer surface of the biological sample holding section 11 to inject the biological sample S and thereafter covering the portion penetrated by the injection needle with grease or the like for encapsulating.

Although a material that can be used for the biological sample holding section 11 according to the embodiment of the present technology is not particularly limited, the biological sample holding section 11 can be formed with resin in the embodiment of the present technology.

In the electrical measuring cartridge 1 according to the embodiment of the present technology, the kind of resin usable in the biological sample holding section 11 is not particularly limited, and one or two or more kinds of resins that can be appropriately applied to the biological sample S may be freely selected and used. For example, a hydrophobic and insulating polymer such as polypropylene, polymethyl methacrylate, polystyrene, acryl, polysulfone, polytetrafluoroethylene, or the like, a copolymer, a blend polymer or the like may be used. In the present technology, in the above-mentioned polymers, in particular, the biological sample holding section 11 may be made of one or more kinds of resins selected from polypropylene, polystyrene, acryl, and polysulfone. Since these resins have a property such as a low coagulation activity with respect to the blood, for example, the container can be appropriately used for measurement in the case when a blood sample is selected as the biological sample S.

(2) Measuring Electrode Unit 12

In the electrical measuring cartridge 1 according to the present technology, the measuring electrode unit 12 is fixed to the biological sample holding section 11, and is composed of a pair of electrodes for electrically measuring the state of the biological sample S. The measuring electrode unit 12 is a part used to be in contact with the biological sample S during electrical measurement and apply the necessary voltage to the biological sample S.

(3) Sedimentation Measuring Electrode Unit 13

In the electrical measuring cartridge 1 according to the present technology, the sedimentation measuring electrode unit 13 is fixed to a position at a different height from the measuring electrode unit 12 of the biological sample holding section 11, and is composed of a pair of electrodes for electrically measuring the degree of sedimentation of sedimenting components. The sedimentation measuring electrode unit 13 is a part used to be in contact with the biological sample S during electrical measurement and apply the necessary voltage to the sedimenting components in the biological sample S.

The measuring electrode unit 12 and the sedimentation measuring electrode unit 13 according to the present technology are made of an electrically conductive material. In the electrical measuring cartridge 1 according to the present technology, the type of the electrically conductive material used for the measuring electrode unit 12 and the sedimentation measuring electrode unit 13 is not particularly limited, and one or two or more materials that can be used for the measurement of an electrical property of the biological sample S may be freely selected for use. Examples include titanium, aluminum, stainless steel, platinum, gold, copper, graphite, and the like. In the present technology, it is particularly preferable to form the measuring electrode unit 12 and/or the sedimentation measuring electrode unit 13 out of an electrically conductive material containing, among the above materials, titanium. Titanium has the property of low coagulation activity on blood, and can therefore be suitably used for measurement etc. in the case where a blood sample is selected as the biological sample S, for example.

The measuring electrode unit 12 and the sedimentation measuring electrode unit 13 will now be described further in detail based on embodiments.

First Embodiment

A first embodiment shown in FIG. 1 is an example in which a pair of measuring electrode units 12 and a pair of sedimentation measuring electrode units 13 are fixed along the inner wall of the biological sample holding section 11, and the pair of sedimentation measuring electrode units 13 are fixed along the inner wall of the biological sample holding section 11 in positions higher than the measuring electrode units 12 fixed to the inner wall of the biological sample holding section 11.

The electrical measuring cartridge 1 according to the present technology includes both the pair of measuring electrode units 12 and the pair of sedimentation measuring electrode units 13, and therefore an electrical property of the measurement target and an electrical property indicating the degree of sedimentation of sedimenting components can be measured independently by one cartridge. For example, in the case where blood is selected as the biological sample S, it is possible to independently measure the blood coagulation time in the measuring electrode unit 12 and the blood sedimentation rate in the sedimentation measuring electrode unit 13. Furthermore, the influence due to the sedimentation of sedimenting components on the measurement result can be excluded on the basis of the obtained measurement result, and the electrical property of the measurement target can be measured more accurately. Thus, the measurement accuracy in electrical measurement can be significantly improved.

Conventional methods include a method in which the degree of sedimentation of sedimenting components is analyzed using an imager or the like and the influence due to the sedimentation of sedimenting components on the measurement result is excluded on the basis of the analysis result, and like methods. However, by using the electrical measuring cartridge 1 according to the present technology, the degree of sedimentation of sedimenting components can be measured without using the imager or the like described above; thus, the electrical measuring cartridge 1 can contribute to the miniaturization of the electrical measuring apparatus, the cost reduction of the apparatus, etc.

Second Embodiment

Figure 2:
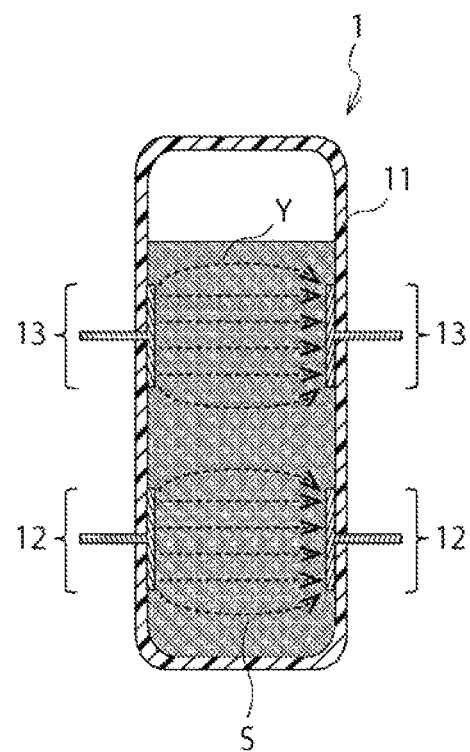
FIG. 2 is a schematic end view schematically showing a second embodiment of an electrical measuring cartridge 1 according to the present technology.

A second embodiment shown in FIG. 2 is an example in which a pair of measuring electrode units 12 and a pair of sedimentation measuring electrode units 13 are fixed along the inner wall of the biological sample holding section 11 apart from each other to such a degree that the lines of electric force (see arrow Y of FIG. 2) do not interfered with each other.

In the present technology, as in the second embodiment shown in FIG. 2, the measuring electrode unit 12 and the sedimentation measuring electrode unit 13 are preferably fixed apart from each other to such a degree that the lines of electric force do not interfere with each other. Thereby, various amounts of electricity measured in the measuring electrode unit 12 and the sedimentation measuring electrode unit 13 can be measured without mutual interference, and the measurement accuracy can be improved.

Third Embodiment

Figure 3:
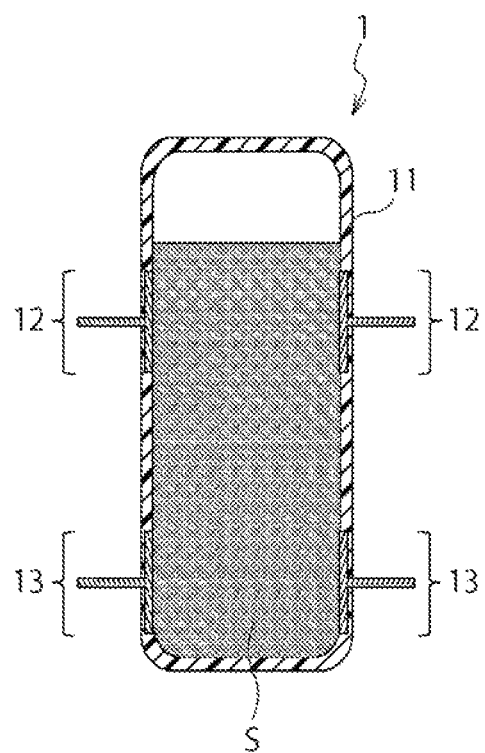
FIG. 3 is a schematic end view schematically showing a third embodiment of an electrical measuring cartridge 1 according to the present technology.

A third embodiment shown in FIG. 3 is an example in which a pair of measuring electrode units 12 are fixed so as to form parts of the inner wall of the biological sample holding section 11 and a pair of sedimentation measuring electrode units 13 are fixed so as to form parts of the inner wall of the biological sample holding section 11 in positions lower than the measuring electrode units 12 fixed to the inner wall of the biological sample holding section 11.

In the present technology, the sedimentation measuring electrode unit 13 is preferably fixed in a position lower than the measuring electrode unit 12 of the biological sample holding section 11. The reason will now be described in detail.

When electrical measurement is started using the electrical measuring cartridge 1 according to the third embodiment, the sedimenting components in the biological sample S sediment gradually over time; when sedimenting components begin to interfere with a portion of a high density of lines of electric force of the sedimentation measuring electrode unit 13, various amounts of electricity such as the impedance and conductance between the sedimentation measuring electrode units 13 begin to change due to the insulating properties of the sedimenting components. The change in various amounts of electricity may be detected by the sedimentation measuring electrode unit 13, and the influence due to the sedimentation over time of sedimenting components on the measurement result can be excluded using the measurement result obtained in the sedimentation measuring electrode unit 13. Thus, the measurement accuracy during electrical measurement is improved. A more detailed description will now be given.

Figure 4:
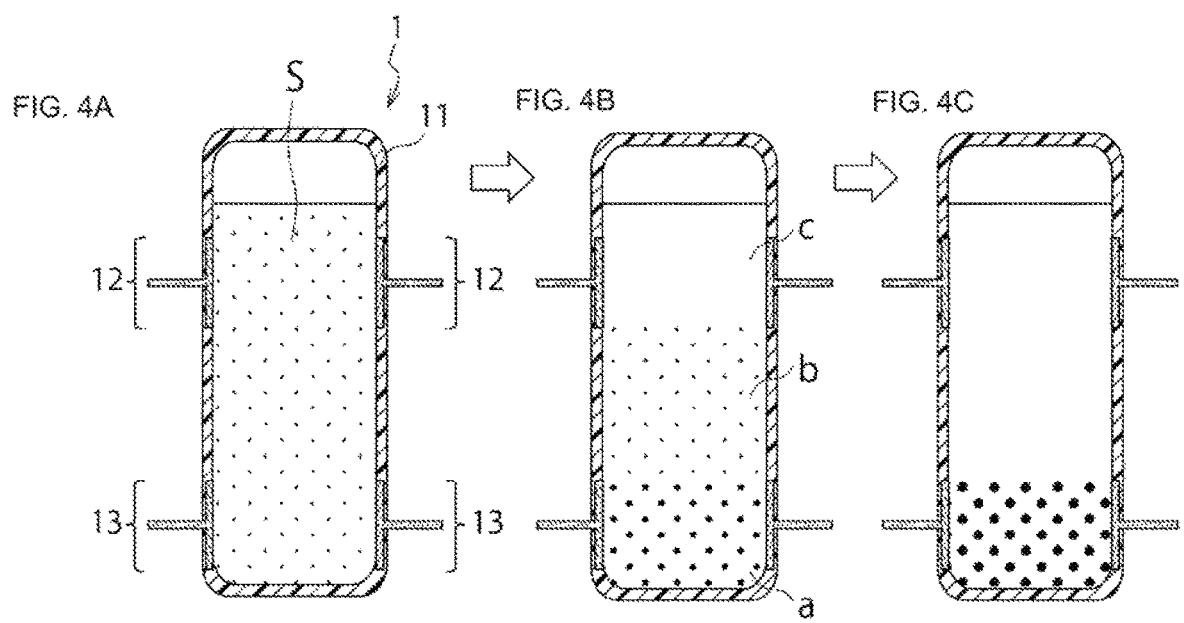
FIG. 4A to 4C are schematic end views schematically showing the relationship between the manner of the sedimentation over time of sedimenting components and the positions of a measuring electrode unit 12 and a sedimentation measuring electrode unit 13.

FIG. 4A to 4C are schematic end views schematically showing the relationship between the manner of the sedimentation over time of sedimenting components and the positions of the measuring electrode unit 12 and the sedimentation measuring electrode unit 13. FIG. 4A shows a state at the start of measurement, FIG. 4B shows a state during the progress of the sedimentation process, and FIG. 4C shows a state at the time of complete sedimentation. In the case of an able-bodied adult person, the whole blood contains a volume fraction of red blood cells of approximately 40%. The red blood cells sediment in a static condition, and are finally deposited in a lower portion of the electrical measuring cartridge 1 as shown in FIG. 4C. On the other hand, mainly blood serum collects in an upper layer portion. As shown in FIG. 4C, during the progress of the sedimentation process, there are roughly three layers of, from the bottom, a red blood cell deposit layer a, a whole blood layer b, and a blood serum layer c.

The change in the conductance between the sedimentation measuring electrode units 13 mainly reflects the amount of deposition of sedimenting components at each time point. In the case where, for example, human blood is selected as the biological sample S, there is not a large difference among individuals in the relationship between the conductance and the amount of deposition of sedimenting components, and the relationship can be predicted in advance and a profile thereof can be prepared. Thus, using the profile, the degree of sedimentation of sedimenting components can be measured from the change over time in the conductance between the sedimentation measuring electrode units 13, and the proportion of blood cell components and the relative position of the human whole blood layer b can be estimated.

Furthermore, the degree of coagulation that does not depend on the degree of blood sedimentation can be calculated from the measurement result of the degree of sedimentation of sedimenting components. Also the concentration and the degree of aggregation of blood can be estimated. Furthermore, it is also possible to support the selection of the model of a dielectric spectrum measured in the measuring electrode unit 12.

Therefore, by using the electrical measuring cartridge 1 according to the present technology, it becomes possible to measure a more accurate amount of electricity in which the influence due to the sedimentation over time of sedimenting components on the measurement result is excluded. Thus, the measurement accuracy in electrical measurement can be improved.

The sedimentation measuring electrode unit 13 is preferably located on the lower side of a position where the cumulative deposition fraction from the portion that forms the bottom during measurement of the biological sample holding section 11 is not less than the volume fraction of the sedimenting components. Thereby, even when the sedimentation of sedimenting components in the biological sample S progresses, the most part of the lines of electric force emitted from the sedimentation measuring electrode unit 13 penetrate through sedimenting components. Therefore, it becomes possible to measure a more accurate degree of sedimentation of sedimenting components in conformity with the change over time.

The measuring electrode unit 12 is preferably located on the upper side of a position where the cumulative volume fraction from the portion that forms the bottom during measurement of the biological sample holding section 11 is not less than the volume fraction of the sedimenting components. Thereby, up until the time when the half of the sedimenting components have sedimented, the most part of the lines of electric force emitted from the measuring electrode unit 12 continuously pass through the measurement target while avoiding the deposit of sedimenting components that deposit over time and the supernatant. Therefore, it becomes possible to obtain a more accurate measurement result.

In the electrical measuring cartridge 1 according to the present technology, the disposition, form, etc. of the measuring electrode unit 12 and the sedimentation measuring electrode unit 13 are not particularly limited, and may be freely designed as appropriate in accordance with the form of the biological sample holding section 11, the measurement method, the electrical measuring apparatus used, etc. to the extent that the necessary voltage can be applied to the biological sample S. In the present technology, particularly in order to improve the measurement efficiency, as shown in the third embodiment of FIG. 3 the connection portions between the biological sample holding section 11, and the measuring electrode unit 12 and the sedimentation measuring electrode unit 13 are preferably in contact with the biological sample S in a planar manner. This is because if, for example, there is a level difference on the inner side wall of the biological sample holding section 11 as shown in the first embodiment of FIG. 1, air bubbles etc. may remain in the level difference portion (see the broken line portion X of FIG. 1) or unevenness of reagent concentration may occur in the level difference portion, and these may adversely influence the measurement value. Hence, the biological sample holding section 11, and the measuring electrode unit 12 and the sedimentation measuring electrode unit 13 may be integrally molded so that their connection portions are smooth as in the third embodiment, and thereby the adverse influence due to air bubbles, sample concentration unevenness, etc. can be excluded; thus, the measurement accuracy in electrical measurement can be improved.

The electrical measuring cartridge 1 according to the present technology may include one or more pairs of measuring electrode units 12 and/or sedimentation measuring electrode units 13. In this case, the measuring electrode units 12 and/or the sedimentation measuring electrode units 13 are preferably disposed parallel in terms of measuring the electrical property of the biological sample S. However, in view of, for example, mold releasability etc. in the case of performing insert molding or the like, the measuring electrode units 12 and/or the sedimentation measuring electrode units 13 may be disposed with several degrees of inclination.

Fourth Embodiment

Figure 5:
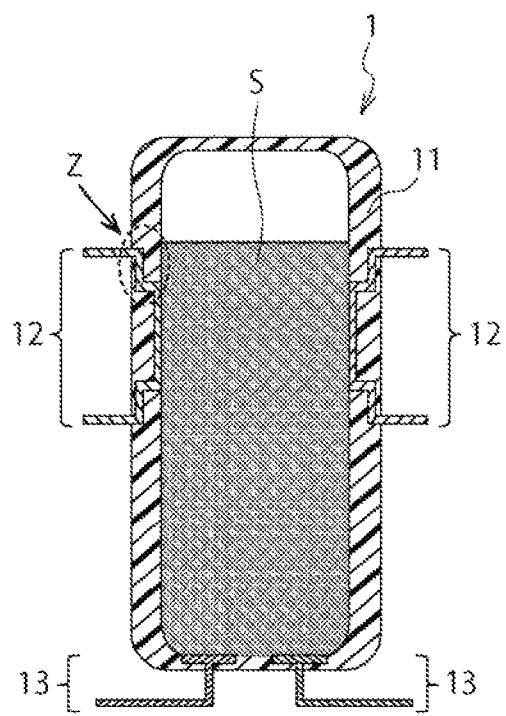
FIG. 5 is a schematic end view schematically showing a fourth embodiment of an electrical measuring cartridge 1 according to the present technology.

A fourth embodiment shown in FIG. 5 is an example in which a pair of measuring electrode units 12 are designed so as to include a bending portion bending in a part of the structure of the portion fixed to the biological sample holding section 11 (see the broken line portion Z of FIG. 5) and a pair of sedimentation measuring electrode units 13 are fixed so as to be located on the bottom surface of the biological sample holding section 11.

In the electrical measuring cartridge 1 according to the present technology, the sedimentation measuring electrode units 13 may be designed so as to face each other as shown in the third embodiment of FIG. 3, or may be designed so as to be located on the bottom surface of the biological sample holding section 11 as shown in the fourth embodiment shown in FIG. 5. However, a design in a facing manner as in the third embodiment provides better sensitivity in electrical measurement, and can improve the measurement accuracy.

Although very rare, there is a case where, due to the difference in strain between the resin and the electrically conductive material etc., the biological sample S leaks out from the boundary portion between the biological sample holding section 11 and the measuring electrode unit 12 and/or the sedimentation measuring electrode unit 13, depending on storage conditions and measurement conditions such as temperature. Thus, by providing the bending portion as shown in the fourth embodiment of FIG. 5, the leakage of the biological sample S out from the boundary between the biological sample holding section 11 and the measuring electrode unit 12 and/or the sedimentation measuring electrode unit 13 can be prevented more reliably than in the third embodiment of FIG. 3 in which the bending portion is not provided.

Furthermore, by the measuring electrode unit 12 and/or the sedimentation measuring electrode unit 13 having the bending portion, the fixation between the biological sample holding section 11 and the measuring electrode unit 12 and/or the sedimentation measuring electrode unit 13 is made firmer, and a sturdy electrical measuring cartridge 1 can be formed.

(4) Liquid Biological Sample S Containing Sedimenting Components

The liquid biological sample S containing sedimenting components that can be used as the measurement target in the present technology is not particularly limited, and may be freely selected. Examples include whole blood and blood plasma, a blood sample containing a blood component such as a diluted solution and/or a chemical agent-added substance of these, and the like. In the case where a blood sample is selected as the biological sample S, the electrical measuring cartridge 1 according to the present technology may be used for the measurement of the state of blood coagulation etc.

(5) Other Matters

In the present technology, the method for fixing the measuring electrode unit 12 and the sedimentation measuring electrode unit 13 to the biological sample holding section 11 is not particularly limited, but is preferably a method of integrally molding the biological sample holding section 11 and the measuring electrode unit 12 and/or the sedimentation measuring electrode unit 13 in a state in which a part of the measuring electrode unit 12 and/or the sedimentation measuring electrode unit 13 is buried in the biological sample holding section 11.

In the case where, for example, the measuring electrode unit 12 and the sedimentation measuring electrode unit 13 are fixed to the biological sample holding section 11 using an adhesive, the adhesive used may, depending on its type, adversely influence the properties of the biological sample S. For example, in the case where blood is selected as the biological sample S, depending on the type of the adhesive used, the blood coagulation activity is promoted and adversely influences the measurement of the objective. However, by employing a method of integrally molding the biological sample holding section 11 and the measuring electrode unit 12 and/or the sedimentation measuring electrode unit 13, that is, a method of not using a fixing material such as an adhesive for the fixation between the biological sample holding section 11 and the measuring electrode unit 12 and/or the sedimentation measuring electrode unit 13, the adverse influence due to a fixing material such as an adhesive on the biological sample S can be excluded. Thus, the measurement accuracy in electrical measurement is improved.

Even if a fixing material having less effect on the biological sample S is used, an adhesion process with the fixing material is added when manufacturing the cartridge for containing a biological sample S, thus raising a problem that productivity is poor. However, when the method of integrally molding the biological sample holding section 11 and the measuring electrode unit 12 and/or the sedimentation measuring electrode unit 13 is employed, the adhesion process does not have to be separately provided, in addition to the molding process of the biological sample holding section 11. As a result, manufacture of the electrical measuring cartridge 1 becomes easier, and the electrical measuring cartridge 1 according to the embodiment of the present technology can be produced at low cost and in large amounts.

Conventional methods include a method in which an electrical property is measured in a state in which an electrode is inserted into a cartridge accommodating a biological sample from the outside, and like methods. However, these methods have a problem that a measurement error occurs due to the difference in the amount of insertion of the electrode into the biological sample. However, by fixing the measuring electrode unit 12 and/or the sedimentation measuring electrode unit 13 to the biological sample holding section 11 in advance, the measurement error due to the difference in the amount of insertion of the electrode into the biological sample can be eliminated. Hence, the measurement accuracy in electrical measurement is improved.

Furthermore, a relative positioning mechanism between an electrode and a cartridge that contains a biological sample, or the like does not have to be disposed to an apparatus side, thus achieving the simplification of a structure on the apparatus side. This can also contribute to the realization of a miniaturized electrical measuring apparatus and a reduced cost of the apparatus, a simplified manufacturing process of the electrical measuring cartridge 1, and the like.

In the present technology, the specific method of integrally molding the biological sample holding section 11 and the measuring electrode unit 12 and/or the sedimentation measuring electrode unit 13 is not particularly limited, and an arbitrary method may be used. For example, in the case where the biological sample holding section 11 is formed of a resin, the measuring electrode unit 12 and/or the sedimentation measuring electrode unit 13 may be disposed in predetermined positions when the resin solidifies from a molten state, and thereby the biological sample holding section 11 and the measuring electrode unit 12 and/or the sedimentation measuring electrode unit 13 can be integrally molded. Specific examples include a method in which the biological sample holding section 11 and the measuring electrode unit 12 and/or the sedimentation measuring electrode unit 13 are integrally molded by what is called insert molding in which the measuring electrode unit 12 and/or the sedimentation measuring electrode unit 13 is inserted into a mold and a resin is injected into the surroundings of the measuring electrode unit 12 and/or the sedimentation measuring electrode unit 13, and thus the measuring electrode unit 12 and/or the sedimentation measuring electrode unit 13 and the resin are integrated, and like methods.

Since the measuring electrode unit 12 and/or the sedimentation measuring electrode unit 13 are fixed concurrently when the biological sample holding section 11 is molded as described above, a manufacturing process of the electrical measuring cartridge 1 can be simplified. Therefore, the electrical measuring cartridge 1 according to the embodiment of the present technology can be produced at low cost and in large amounts.

The electrical measuring cartridge 1 according to the embodiment of the present technology can be produced at low cost and in large amounts as described above. Taking advantage of such characteristics, for example, the electrical measuring cartridge 1 according to the embodiment of the present technology may be configured as being disposable. When the electrical measuring cartridge 1 according to the embodiment of the present technology is configured as being disposable, time and labor such as washing of a cartridge can be saved, thus achieving the efficient measurement. Also, measurement error due to another biological sample S remained in the cartridge can be inhibited from occurring, thus also realizing the improvement of measurement accuracy during electrical measurement.

2. Electrical Measuring Apparatus 10 for Biological Sample

Figure 6:
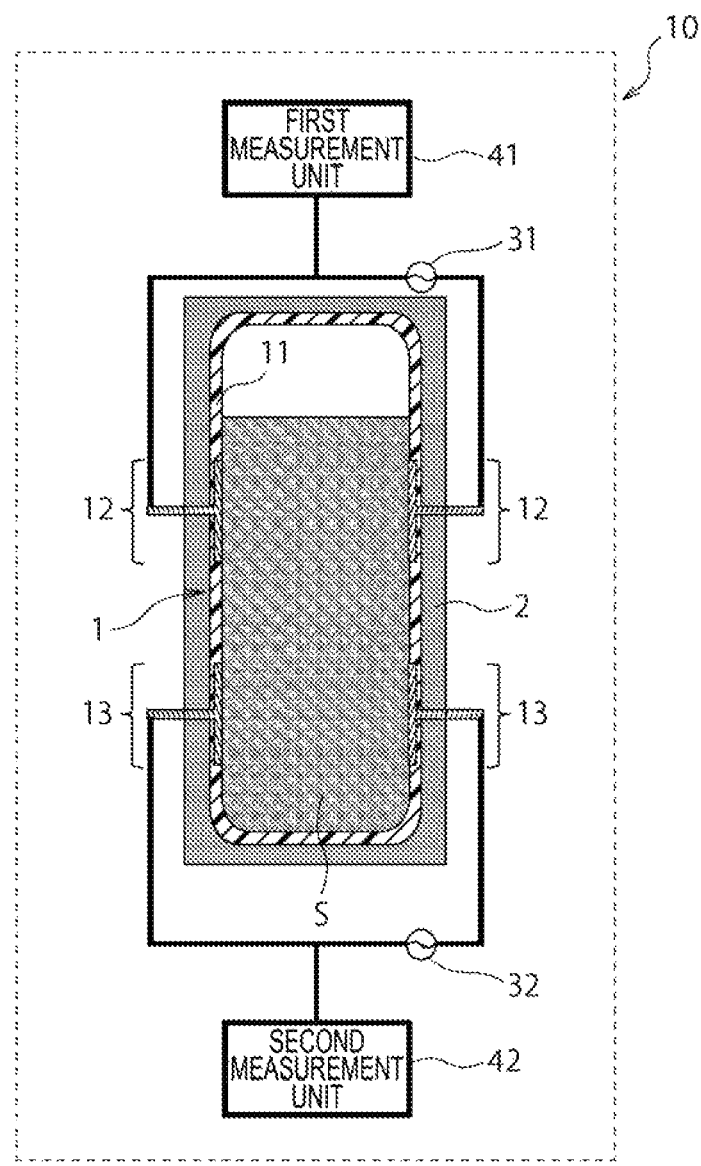
FIG. 6 is a schematic conceptual diagram schematically showing a first embodiment of an electrical measuring apparatus 10 for a biological sample according to the present technology.

FIG. 6 is a schematic conceptual diagram schematically showing a first embodiment of an electrical measuring apparatus 10 for a biological sample according to the present technology. This embodiment uses the electrical measuring cartridge 1 according to the third embodiment described above. The electrical measuring apparatus 10 for a biological samples according to the present technology roughly includes at least the electrical measuring cartridge 1 described above, a cartridge holding section 2, a first application unit 31, a second application unit 32, a first measurement unit 41, and a second measurement unit 42. Each part will now be described in detail. The electrical measuring cartridge 1 is similar to that described above, and a description is omitted herein.

(1) Cartridge Holding Section 2

The cartridge holding section 2 is a part that holds the electrical measuring cartridge 1 according to the present technology. The cartridge holding section 2 may be freely designed as appropriate in accordance with the form of the electrical measuring cartridge 1 etc.

The cartridge holding section 2 may include a temperature adjustment mechanism. The temperature adjustment mechanism is a mechanism that can keep constant the temperature of the biological sample S held in the biological sample holding section 11. Specific examples include a method in which the temperature adjustment mechanism is formed of a material that can keep the cartridge holding section 2 warm, and thereby the temperature of the biological sample S is made constant in a state in which the electrical measuring cartridge 1 according to the present technology is held in the electrical measuring apparatus 10 for a biological sample, and like methods.

(2) First Application Unit 31

The first application unit 31 is a part that applies a voltage to the measuring electrode unit 12 of the electrical measuring cartridge 1 according to the present technology. Specifically, with a time point when an instruction to start measurement is received or a time point when the electrical measuring apparatus 10 for a biological sample is supplied with electric power as the starting time point, the first application unit 31 applies a voltage to the measuring electrode unit 12 of the electrical measuring cartridge 1. In this case, the first application unit 31 applies an alternating current voltage with a predetermined frequency to the measuring electrode unit 12 at set measuring intervals. The voltage that the first application unit 31 applies may be also a direct current voltage, depending on the electrical property to be measured.

(3) Second Application Unit 32

The second application unit 32 is a part that applies a voltage to the sedimentation measuring electrode unit 13 of the electrical measuring cartridge 1 according to the present technology. The specific method for applying a voltage etc. are similar to those of the first application unit 31, and a description is omitted herein.

It is also possible to design the electrical measuring apparatus 10 for a biological sample according to the present technology in such a manner that the roles of the first application unit 31 and the second application unit 32 can be played by one application unit.

(4) First Measurement Unit 41

The first measurement unit 41 is a part that measures the electrical property obtained from the measuring electrode unit 12. Specifically, with a time point when an instruction to start measurement is received or a time point when the electrical measuring apparatus 10 for a biological samples is supplied with electric power as the starting time point, an electrical property such as complex permittivity (hereinafter, occasionally referred to as simply "permittivity") or the frequency dispersion thereof is measured. For example, in the case where the permittivity is measured, the first measurement unit 41 measures the current or impedance between the measuring electrode units 12 of the electrical measuring cartridge 1 in a predetermined period, and derives the permittivity from the measurement value. For the derivation of the permittivity, a known function or relation that expresses a relationship between current or impedance and permittivity may be used.

(5) Second Measurement Unit 42

The second measurement unit 42 is a part that measures the electrical property obtained from the sedimentation measuring electrode unit 13. The specific method for measuring the electrical property etc. are similar to those of the first measurement unit 41, and a description is omitted herein.

It is also possible to design the electrical measuring apparatus 10 for a biological samples according to the present technology in such a manner that the roles of the first measurement unit 41 and the second measurement unit 42 can be played by one measurement unit.

(6) Correction Section 5

Figure 7:
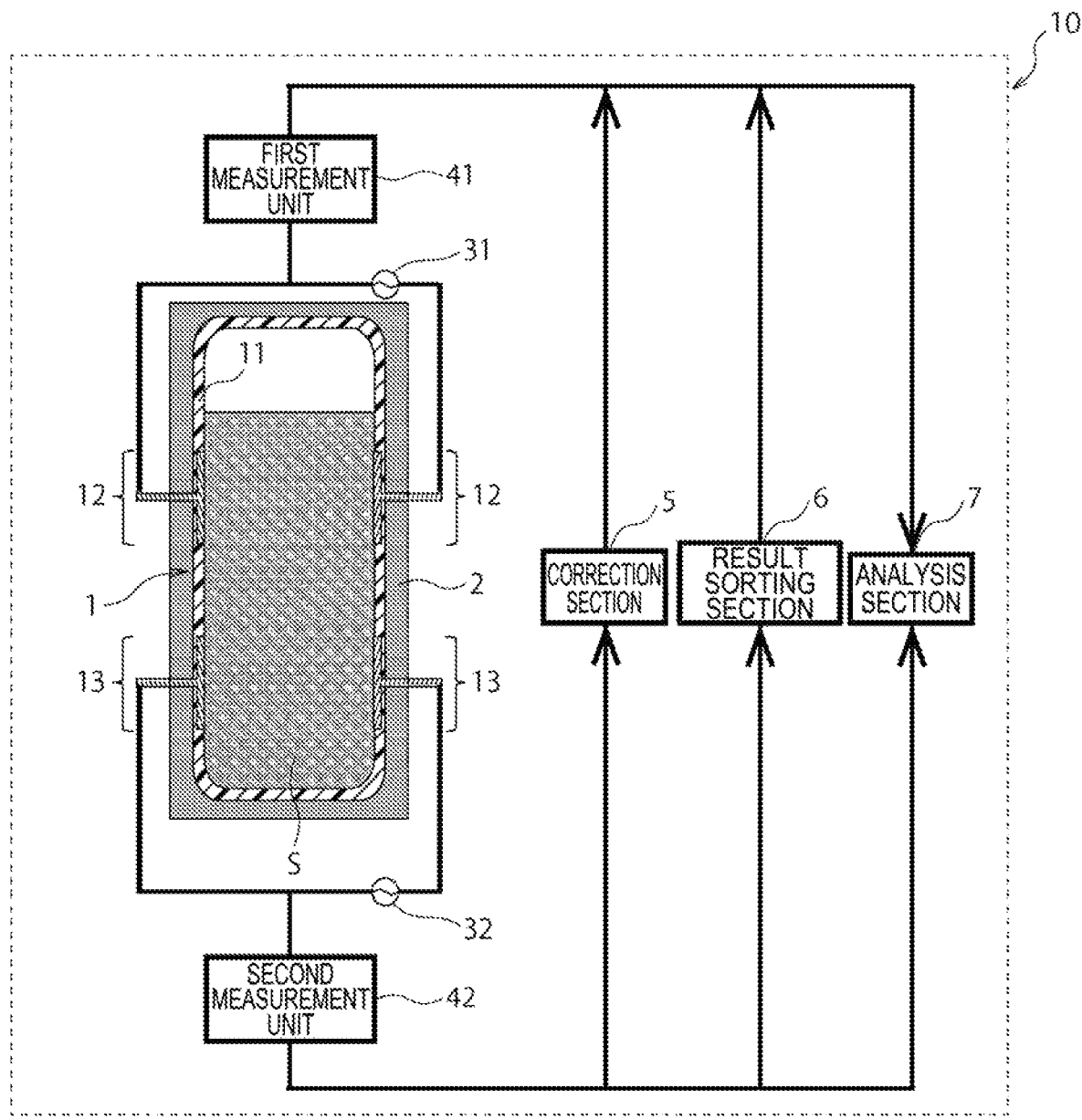
FIG. 7 is a schematic conceptual diagram schematically showing a second embodiment of an electrical measuring apparatus 10 for a biological sample according to the present technology.

As shown in a second embodiment of FIG. 7, the electrical measuring apparatus 10 for biological sample according to the present technology may include a correction section 5 as necessary. The correction section 5 is a part that corrects the measurement result obtained from the first measurement unit 41 using the measurement result obtained from the second measurement unit 42. Specifically, on the basis of the measurement result obtained from the second measurement unit 42 that shows the degree of sedimentation of sedimenting components, the measurement result obtained from the first measurement unit 41 is corrected to a value in which the influence due to the sedimentation of sedimenting components is excluded. Thereby, the artifact due to the sedimentation of sedimenting components can be reduced, and the measurement accuracy in electrical measurement can be improved.

(7) Result Sorting Section 6

As shown in the second embodiment of FIG. 7, the electrical measuring apparatus 10 for a biological sample according to the present technology may include a result sorting section 6 as necessary. The result sorting section 6 is a part that sorts the measurement result obtained from the first measurement unit 41 using the measurement result obtained from the second measurement unit 42. Specifically, the measurement result obtained from the first measurement unit 41 is sorted on the basis of the measurement result obtained from the second measurement unit 42 that shows the degree of sedimentation of sedimenting components. Examples include a method of issuing an alert to a measurement result that does not conform to a reference value, a method of deleting a measurement result as necessary, and like methods. Thereby, the user's convenience is improved, and also the measurement accuracy in electrical measurement is improved.

(8) Other Matters

In the electrical measuring apparatus 10 for a biological samples according to the present technology, the measurement in the first measurement unit 41 and the measurement in the second measurement unit 42 may be performed at different timings. Specifically, for example, first the measurement in the first measurement unit 41 is started, and next the measurement in the second measurement unit 42 is started. Thereby, the lines of electric force of the measuring electrode unit 12 and the sedimentation measuring electrode unit 13 are prevented from interfering with each other; thus, the measurement accuracy in electrical measurement can be improved.

Further, in the electrical measuring apparatus 10 for a biological samples according to the present technology, the measurement in the first measurement unit 41 and the measurement in the second measurement unit 42 may be performed with different frequencies. Thereby, electrical measurement can be performed efficiently and quickly, and also the measurement accuracy is improved. The reason will now be described in detail.

A description is given on the supposition that a blood sample is selected as the biological sample S. In the case where, for example, the degree of blood coagulation (clot of blood) is measured in the first measurement unit 41, a preferred frequency range of the first measurement unit 41 is 3 MHz to 15 MHz. In this case, the degree of blood sedimentation is measured in the second measurement unit 42; a preferred frequency range of the second measurement unit 42 is 100 kHz to 40 MHz. Hence, by setting, for example, the frequency of the first measurement unit 41 to 15 MHz and the frequency of the second measurement unit 42 to 100 kHz, the influence on both measurement units due to the frequency being almost equal between both measurement units can be excluded, and the error on the measurement result can be reduced. Thus, the measurement accuracy in electrical measurement is improved. Furthermore, since the measurement in the first measurement unit 41 and the measurement in the second measurement unit 42 can be performed concurrently, it becomes possible to perform electrical measurement efficiently and quickly.

Further, the electrical measuring apparatus 10 for a biological samples according to the present technology may include a feedback control mechanism, which is not illustrated in the drawings. The feedback control mechanism is a mechanism that can alter the measurement conditions of the first measurement unit 41 to more appropriate measurement conditions using the measurement result obtained in the second measurement unit 42. Specifically, on the basis of the measurement result obtained from the second measurement unit 42 that shows the degree of sedimentation of sedimenting components, the measurement conditions of the first measurement unit 41 are altered to more appropriate measurement conditions in which the influence due to the sedimentation of sedimenting components is excluded. Thereby, the user's convenience in electrical measurement is improved, and also the measurement accuracy is improved.

In addition, the electrical measuring apparatus 10 for a biological samples according to the present technology may include a positioning mechanism of the electrical measuring cartridge 1 according to the present technology. By accurately setting the position of the electrical measuring cartridge 1, also the contact positions between the measuring electrode unit 12 and the first application unit 31 and between the sedimentation measuring electrode unit 13 and the second application unit 32 etc. are made accurate, and the user's convenience and the measurement accuracy are improved. Specific examples include a method of designing positioning pins that position the electrical measuring cartridge 1 in the height direction with respect to the electrical measuring apparatus 10 for a biological samples, and like methods.

Further, as shown in the second embodiment of FIG. 7, the electrical measuring apparatus 10 for a biological sample may include an analysis section 7 that receives electrical property data of the biological sample S derived from the first measurement unit 41 and the second measurement unit 42 and performs the determination of a physical property of the biological sample S etc.

Specifically, electrical property data of the biological sample S derived from the first measurement unit 41 and the second measurement unit 42 are given to the analysis section 7 at measuring intervals; and upon receiving the electrical property data given from the first measurement unit 41 and the second measurement unit 42, the analysis section 7 starts the determination of a physical property of the biological sample S etc. Further, the analysis section 7 notifies the result of determination of the physical property etc. of the biological sample S and/or permittivity data. This notification may be performed by, for example, making a graph and displaying it on a monitor or printing it on a certain medium.

3. Electrical Measuring System 20 for Biological Sample

Figure 8:
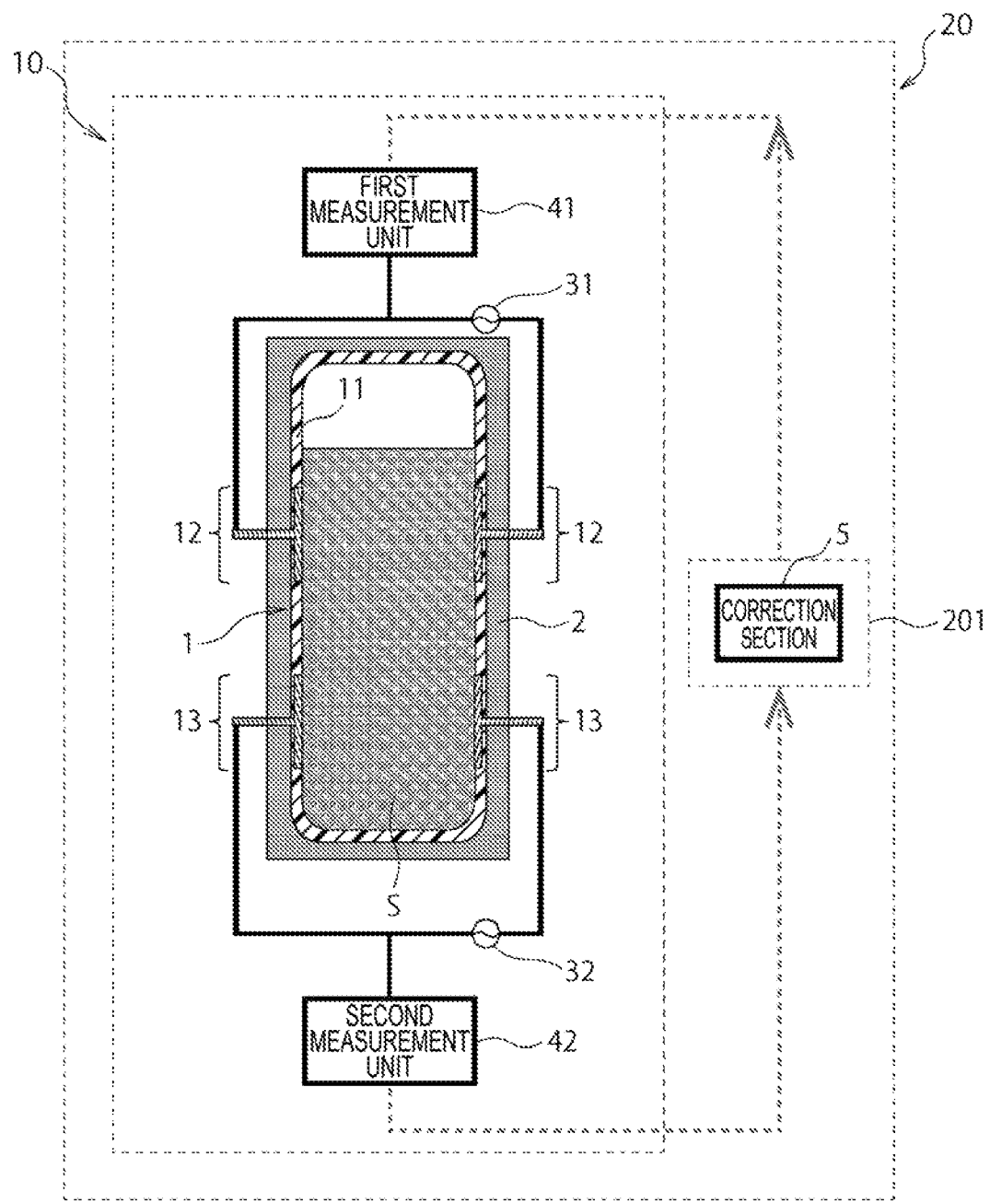
FIG. 8 is a schematic conceptual diagram schematically showing a first embodiment of an electrical measuring system 20 for a biological sample according to the present technology.
Figure 9:
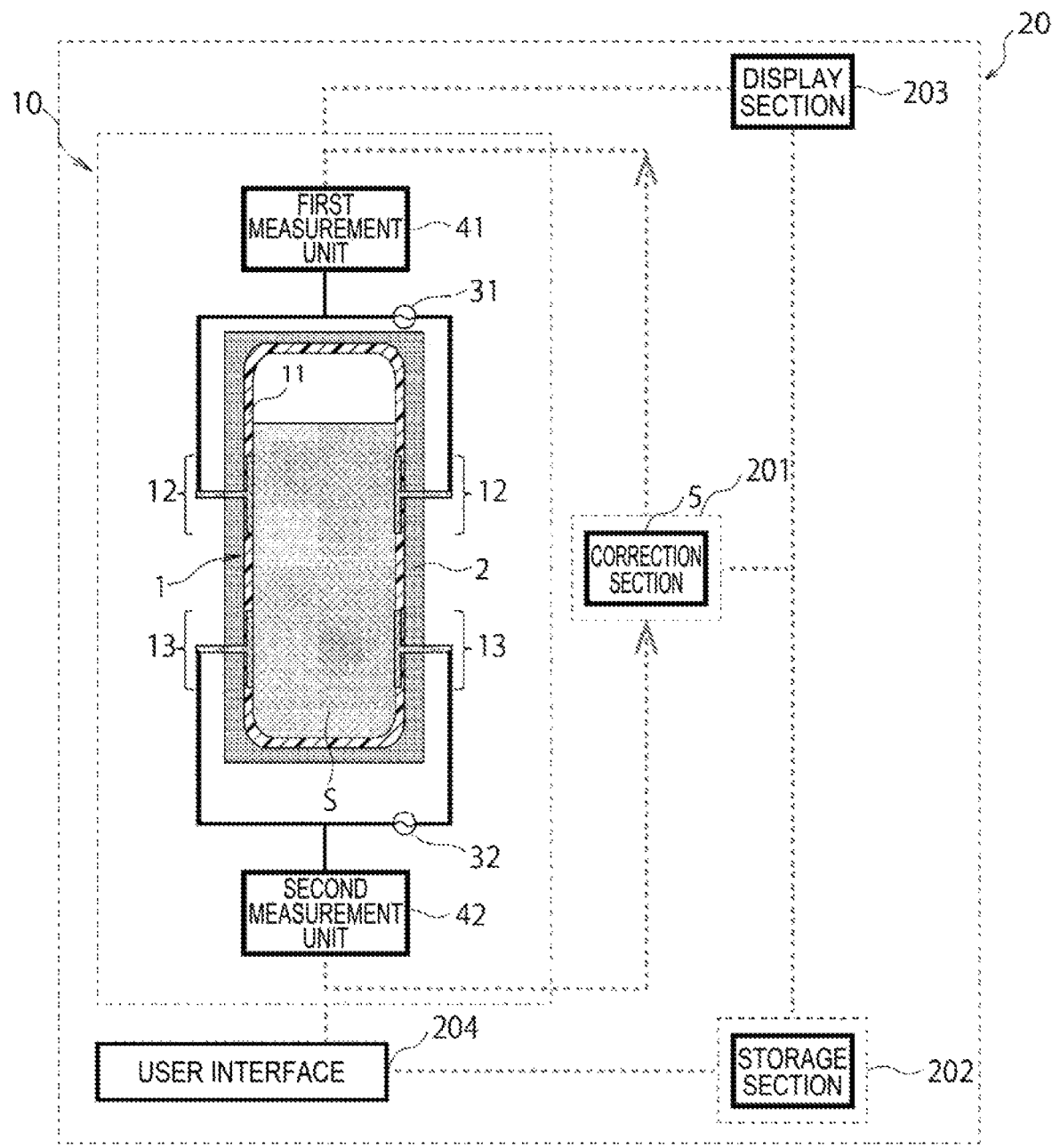
FIG. 9 is a schematic conceptual diagram schematically showing a second embodiment of an electrical measuring system 20 for a biological sample according to the present technology.

FIG. 8 is a schematic conceptual diagram schematically showing a first embodiment of an electrical measuring system 20 for a biological sample according to the present technology. This embodiment uses the electrical measuring cartridge 1 according to the third embodiment described above and the electrical measuring apparatus 10 for a biological sample according to the first embodiment. The electrical measuring system 20 for a biological sample according to the present technology roughly includes at least the electrical measuring apparatus 10 for a biological sample described above and an analysis device 201. As shown in a second embodiment of FIG. 9, the electrical measuring system 20 for a biological sample may further include a server 202, a display section 203, a user interface 204, etc. as necessary. Each part will now be described in detail. The electrical measuring apparatus 10 for a biological sample is similar to that described above, and a description is omitted herein.

(1) Analysis Device 201

The analysis device 201 according to the present technology includes at least the correction section 5. That is, the electrical measuring system 20 for a biological sample according to the present technology supposes a structure in which the correction section 5 described above is present outside the electrical measuring apparatus 10 for a biological sample. Thereby, even in a place apart from the electrical measuring apparatus 10 for a biological sample, on the basis of the measurement result obtained from the second measurement unit 42 that shows the degree of sedimentation of sedimenting components, the measurement result obtained from the first measurement unit 41 can be corrected to a value in which the influence due to the sedimentation of sedimenting components is excluded. Therefore, the user's convenience in electrical measurement is improved, and also the measurement accuracy is improved. The correction section 5 is similar to that described above, and a description is omitted herein.

The analysis device 201 may further include the result sorting section 6 and the analysis section 7 described above.

In the electrical measuring system 20 for a biological sample according to the present technology, the electrical measuring apparatus 10 for a biological sample and the analysis device 201 may be connected via a network. Thereby, remote manipulation becomes possible, and therefore the user's convenience is improved.

(2) Server 202

The server 202 includes a storage section that stores the measurement result obtained in the electrical measuring apparatus 10 for a biological sample and/or the analysis result obtained in the analysis device 201. A plurality of servers 202 may be provided individually for the electrical measuring apparatus 10 for abiological sample and the analysis device 201, or all the results may be stored in one server 202.

(3) Display Section 203

The display section 203 is a part that displays the measurement result obtained in the electrical measuring apparatus 10 for a biological sample, the analysis result obtained in the analysis device 201, etc. A plurality of display sections 203 may be provided individually for the data and results to be displayed, or all the data and results may be displayed on one display section 203.

(4) User Interface 204

The user interface 204 is a part for the user's manipulation. The user can access each part of the electrical measuring system 20 for a biological sample according to the present technology through the user interface 204.

In the electrical measuring system 20 for a biological sample according to the present technology, also the server 202, the display section 203, and the user interface 204 may be connected to the electrical measuring apparatus 20 for a biological sample via a network, similarly to the analysis device 201. Thereby, remote manipulation becomes possible, and therefore the user's convenience is improved.

4. Electrical Measuring Kit K for Biological Sample

Figure 10:
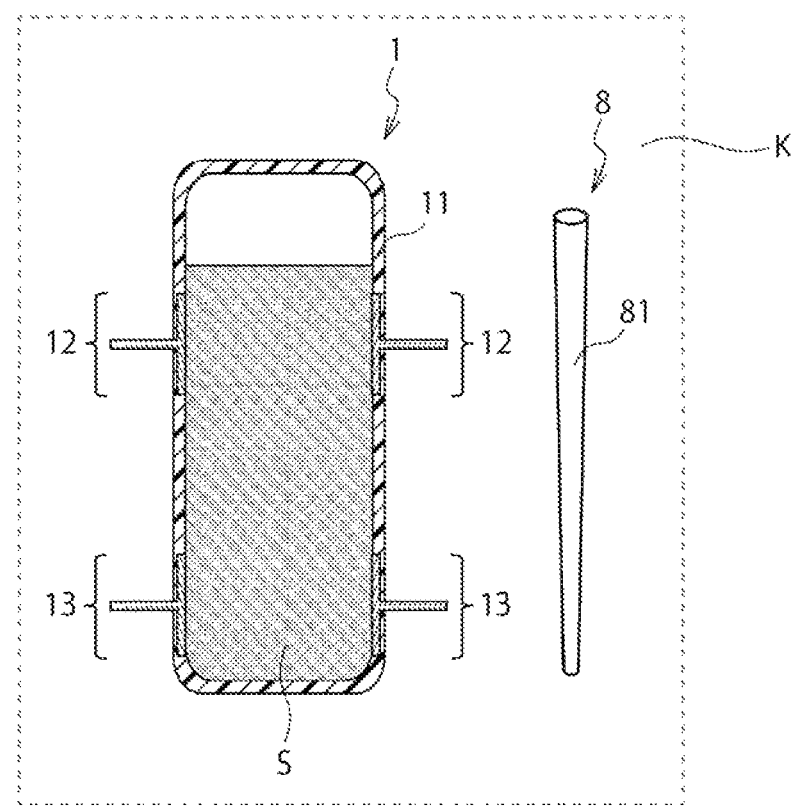
FIG. 10 is a schematic diagram schematically showing a first embodiment of an electrical measuring kit K for a biological sample according to the present technology.

FIG. 10 is a schematic diagram schematically illustrating a first embodiment of an electrical measuring kit K according to an embodiment of the present technology. In this embodiment, the previously-described electrical measuring cartridge 1 according to the third embodiment is used. The electrical measuring kit K according to the embodiment of the present technology roughly includes at least the previously-described electrical measuring cartridge 1, and a biological sample introducing member 8. Hereinafter, it will be described in detail. It is noted that the electrical measuring cartridge 1 is similar to that previously described, and therefore description thereof is omitted here.

(1) Biological Sample Introducing Member 8

The biological sample introducing member 8 is a member configured to introduce the biological sample S into the biological sample holding section 11. An example thereof may include a tip 81 having a pipette shape, as illustrated in a first embodiment of FIG. 10. More specifically, a suction mechanism (for example, a pipetter) is disposed to the previously-described electrical measuring apparatus 10 for a biological sample, and the tip 81 is attached to the suction mechanism, thereby enabling the biological sample S to be introduced.

The biological sample introducing member 8 according to the embodiment of the present technology is not limited to the tip 81 having a pipette shape illustrated as an example in FIG. 10, and may be freely selected depending on the type of the biological sample S, the measurement method, the electrical measuring apparatus to be used, and the like, as long as it is the whole or a portion of a tool with which the biological sample S can be introduced into the biological sample holding section 11. Another example thereof may include an injection needle, other than the tip 81 having a pipette shape.

The biological sample introducing member 8 may be configured as being disposable, in a similar manner to the electrical measuring cartridge 1. When the biological sample S introducing member 8 is configured as being disposable, time and labor such as washing of a tool used for the introduction of a biological sample can be saved, thus achieving the improvement of user's convenience and the efficient measurement of electrical properties. Also, measurement error due to another biological sample S remained in the tool used for the introduction of a biological sample can be inhibited from occurring, thus also realizing the improvement of measurement accuracy during electrical measurement.

5. Electrical Measuring Method for Biological Sample

The electrical measuring cartridge 1 according to the embodiment of the present technology may be appropriately used to measure the electrical properties of the biological sample S. The electrical properties that can be measured through an electrical measuring method for a biological sample according to the embodiment of the present technology are not particularly limited but may be freely measured according to the kind of the biological sample S, which is the measurement target, or physical properties to be analyzed. For example, permittivity, impedance, or the like, can be measured.

Using the electrical measuring method for a biological sample according to the embodiment of the present technology, for example, when the blood is selected as the biological sample S, a blood coagulation situation or a blood sedimentation situation can be analyzed from the measurement value of the permittivity or impedance. More specifically, for example, a parameter showing characteristics from a plurality of permittivity and/or impedance measurement values received during the analysis period can be derived, and the blood coagulation situation or the blood sedimentation situation can be analyzed based on comparison of the parameter with a reference value that determines a reference of acceleration of blood coagulability or progress of a blood sedimentation process. As a result, the measurement accuracy when measuring electrical properties improves.

The electrical measuring method for a biological sample according to the present technology may further perform a first application step of applying a voltage to the measuring electrode unit 12, a second application step of applying a voltage to the sedimentation measuring electrode unit 13, a first measurement step of measuring the electrical property obtained from the measuring electrode unit 12, and a second measurement step of measuring the electrical property obtained from the sedimentation measuring electrode unit 13. Thereby, in the case where, for example, blood is selected as the biological sample S, it becomes possible to measure the blood sedimentation rate in the second measurement step and the time of blood coagulation in the first measurement step. Therefore, the correction of the measurement result obtained from the first measurement step etc. become possible on the basis of the measurement result obtained from the second measurement step. Thus, the measurement accuracy in electrical measurement can be further improved.

Additionally, the present technology may also be configured as below.

(1)

An electrical measuring cartridge including at least:

a biological sample holding section that accommodates a liquid biological sample containing a sedimenting component;

a measuring electrode unit that is fixed to the biological sample holding section and composed of a pair of electrodes for electrically measuring a state of the biological sample; and a sedimentation measuring electrode unit that is fixed to a position at a different height from the measuring electrode unit of the biological sample holding section and composed of a pair of electrodes for electrically measuring a degree of sedimentation of the sedimenting component.

(2)

The electrical measuring cartridge according to (1), wherein the measuring electrode unit and the sedimentation measuring electrode unit are fixed apart from each other to such a degree that mutual lines of electric force do not interfere with each other.

(3)

The electrical measuring cartridge according to (1) or (2), wherein the sedimentation measuring electrode unit is fixed to a position lower than the measuring electrode unit of the biological sample holding section.

(4)

The electrical measuring cartridge according to (3), wherein the sedimentation measuring electrode unit is located on a lower side of a position where a cumulative deposition fraction from a portion that forms a bottom during measurement of the biological sample holding section is not less than a volume fraction of the sedimenting component.

(5)

The electrical measuring cartridge according to any of (1) to (4), wherein the measuring electrode unit is located on an upper side of a position where a cumulative deposition fraction from a portion that forms a bottom during measurement of the biological sample holding section is not less than a volume fraction of the sedimenting component.

(6)

The electrical measuring cartridge according to any of (1) to (5), wherein the biological sample holding section is made of resin.

(7)

The electrical measuring cartridge according to (6), wherein the resin is one or more kinds of resin selected from polypropylene, polystyrene, acryl, and polysulfone.

(8)

The electrical measuring cartridge according to any of (1) to (7), wherein the biological sample is a blood sample.

(9)

The electrical measuring cartridge according to (8), wherein the electrical measuring cartridge is used for measurement of a state of blood coagulation.

(10)

An electrical measuring apparatus for a biological sample, the electrical measuring apparatus including at least:

a cartridge holding section that holds an electrical measuring cartridge including at least a biological sample holding section that accommodates a liquid biological sample containing a sedimenting component, a measuring electrode unit that is fixed to the biological sample holding section and composed of a pair of electrodes for electrically measuring a state of the biological sample, and a sedimentation measuring electrode unit that is fixed to a position at a different height from the measuring electrode unit of the biological sample holding section and composed of a pair of electrodes for electrically measuring a degree of sedimentation of the sedimenting component;

a first application unit that applies a voltage to the measuring electrode unit;

a second application unit that applies a voltage to the sedimentation measuring electrode unit;

a first measurement unit that measures an electrical property obtained from the measuring electrode unit; and a second measurement unit that measures an electrical property obtained from the sedimentation measuring electrode unit.

(11)

The electrical measuring apparatus for a biological sample according to (10), including a correction section that corrects a measurement result obtained from the first measurement unit using a measurement result obtained from the second measurement unit.

(12)

The electrical measuring apparatus for a biological sample according to (10) or (11), including a result sorting section that sorts a measurement result obtained from the first measurement unit using a measurement result obtained from the second measurement unit.

(13)

The electrical measuring apparatus for a biological sample according to any of (10) to (12), wherein measurement in the first measurement unit and measurement in the second measurement unit are performed at different timings.

(14)

The electrical measuring apparatus for a biological sample according to any of (10) to (13), wherein measurement in the first measurement unit and measurement in the second measurement unit are performed with different frequencies.

(15)

An electrical measuring system for a biological sample, the electrical measuring system including at least:

an electrical measuring apparatus for a biological sample, including at least a cartridge holding section for holding an electrical measuring cartridge, including at least a biological sample holding section that accommodates a liquid biological sample containing a sedimenting component, a measuring electrode unit that is fixed to the biological sample holding section and composed of a pair of electrodes for electrically measuring a state of the biological sample, and a sedimentation measuring electrode unit that is fixed to a position at a different height from the measuring electrode unit of the biological sample holding section and composed of a pair of electrodes for electrically measuring a degree of sedimentation of the sedimenting component, a first application unit that applies a voltage to the measuring electrode unit, a second application unit that applies a voltage to the sedimentation measuring electrode unit, a first measurement unit that measures an electrical property obtained from the measuring electrode unit, and a second measurement unit that measures an electrical property obtained from the sedimentation measuring electrode unit; and an analysis device that includes at least a correction section that corrects a measurement result obtained from the first measurement unit using a measurement result obtained from the second measurement unit.

(16)

The electrical measuring system for a biological sample according to (15), wherein the electrical measuring apparatus for a biological sample and the analysis device are connected via a network.

(17)

An electrical measuring method for a biological sample, the electrical measuring method including:

measuring an electrical property of the biological sample using an electrical measuring cartridge including at least a biological sample holding section that accommodates a liquid biological sample containing a sedimenting component, a measuring electrode unit that is fixed to the biological sample holding section and composed of a pair of electrodes for electrically measuring a state of the biological sample, and a sedimentation measuring electrode unit that is fixed to a position at a different height from the measuring electrode unit of the biological sample holding section and composed of a pair of electrodes for electrically measuring a degree of sedimentation of the sedimenting component.

(18) The electrical measuring method for a biological sample according to (17), including at least:
a first application step of applying a voltage to the measuring electrode unit;
a second application step of applying a voltage to the sedimentation measuring electrode unit;
a first measurement step of measuring an electrical property obtained from the measuring electrode unit; and
a second measurement step of measuring an electrical property obtained from the sedimentation measuring electrode unit.

REFERENCE SIGNS LIST 1 electrical measuring cartridge
11 biological sample holding section
12 measuring electrode unit
13 sedimentation measuring electrode unit
10 electrical measuring apparatus for biological sample
2 cartridge holding section
31 first application unit
32 second application unit
41 first measurement unit
42 second measurement unit
5 correction section
6 result sorting section
7 analysis section
20 electrical measuring system for biological sample
201 analysis device
202 server
203 display section
204 user interface
S liquid biological sample containing sedimenting components
K electrical measuring kit for biological sample
8 biological sample introducing member
81 pipette-shaped tip

The invention claimed is:

1. An electrical measuring cartridge, comprising:
a biological sample holding section that accommodates a liquid biological sample containing a sedimenting component;
a measuring electrode unit fixed to the biological sample holding section, wherein:
the measuring electrode unit comprises a first pair of electrodes, and
the first pair of electrodes electrically measures a state of the liquid biological sample; and
a sedimentation measuring electrode unit fixed to a first position at a height different from a height of the measuring electrode unit of the biological sample holding section, wherein:
the sedimentation measuring electrode unit comprises second pair of electrodes,
the second pair of electrodes electrically measures a degree of sedimentation of the sedimenting component, and
the measuring electrode unit and the sedimentation measuring electrode unit are fixed as parts of an inner wall of the biological sample holding section.

2. The electrical measuring cartridge according to claim 1, wherein the measuring electrode unit is fixed apart from the sedimentation measuring electrode unit such that lines of electric force of the measuring electrode unit do not interfere with lines of electric force of the sedimentation measuring electrode unit.

3. The electrical measuring cartridge according to claim 1, wherein the first position of the sedimentation measuring electrode unit is lower than a second position of the measuring electrode unit of the biological sample holding section.

4. The electrical measuring cartridge according to claim 3, wherein the sedimentation measuring electrode unit is located on a lower side of a third position where a cumulative deposition fraction, from a portion that forms a bottom during measurement of the biological sample holding section, is not less than a volume fraction of the sedimenting component.

5. The electrical measuring cartridge according to claim 1, wherein the measuring electrode unit is located on an upper side of a third position where a cumulative deposition fraction, from a portion that forms a bottom during measurement of the biological sample holding section, is not less than a volume fraction of the sedimenting component.

6. The electrical measuring cartridge according to claim 1, wherein the biological sample holding section is of resin.

7. The electrical measuring cartridge according to claim 6, wherein the resin is at least one of polypropylene, polystyrene, acryl, or polysulfone.

8. The electrical measuring cartridge according to claim 1, wherein the liquid biological sample is a blood sample.

9. The electrical measuring cartridge according to claim 8, wherein the electrical measuring cartridge is for measurement of a state of blood coagulation.

10. An electrical measuring apparatus, comprising:
a cartridge holding section that holds an electrical measuring cartridge, wherein the electrical measuring cartridge includes:
a biological sample holding section that accommodates a liquid biological sample containing a sedimenting component,
a measuring electrode unit that is fixed to the biological sample holding section, wherein:
the measuring electrode unit comprises a first pair of electrodes, and
the first pair of electrodes electrically measures a state of the liquid biological sample, and
a sedimentation measuring electrode unit that is fixed to a position at a height different from a height of the measuring electrode unit of the biological sample holding section, wherein:
the sedimentation measuring electrode unit comprises a second pair of electrodes;
the second pair of electrodes electrically measures a degree of sedimentation of the sedimenting component, and
the measuring electrode unit and the sedimentation measuring electrode unit are fixed as parts of an inner wall of the biological sample holding section;
a first application unit configured to apply a first voltage to the measuring electrode unit;
a second application unit configured to apply a second voltage to the sedimentation measuring electrode unit;
a first measurement unit configured to measure an electrical property obtained from the measuring electrode unit; and
a second measurement unit configured to measure an electrical property obtained from the sedimentation measuring electrode unit.

11. The electrical measuring apparatus according to claim 10, further comprising
a correction section configured to correct a measurement result obtained from the first measurement unit based on a measurement result obtained from the second measurement unit.

12. The electrical measuring apparatus according to claim 10, further comprising
a result sorting section configured to sort a measurement result obtained from the first measurement unit based on a measurement result obtained from the second measurement unit.

13. The electrical measuring apparatus according to claim 10, wherein:
the measurement in the first measurement unit is at a first time,
the measurement in the second measurement unit is at a second time, and
the first time is different from the second time.

14. The electrical measuring apparatus according to claim 10, wherein:
the measurement in the first measurement unit is at a first frequency,
the measurement in the second measurement unit is at a second frequency, and
the first frequency is different from the second frequency.

15. An electrical measuring system, comprising:
an electrical measuring apparatus, including
a cartridge holding section that holds an electrical measuring cartridge, wherein the electrical measuring cartridge includes:
a biological sample holding section that accommodates a liquid biological sample containing a sedimenting component;
a measuring electrode unit that is fixed to the biological sample holding section, wherein:
the measuring electrode unit comprises a first pair of electrodes, and
the first pair of electrodes electrically measures a state of the liquid biological sample, and
a sedimentation measuring electrode unit that is fixed to a position at a height different from a height of the measuring electrode unit of the biological sample holding section, wherein:
the sedimentation measuring electrode unit comprises a second pair of electrodes,
the second pair of electrodes electrically measures a degree of sedimentation of the sedimenting component, and
the measuring electrode unit and the sedimentation measuring electrode unit are fixed as parts of an inner wall of the biological sample holding section;
a first application unit configured to apply a first voltage to the measuring electrode unit;
a second application unit configured to apply a second voltage to the sedimentation measuring electrode unit;
a first measurement unit configured to measure an electrical property obtained from the measuring electrode unit; and
a second measurement unit configured to measure an electrical property obtained from the sedimentation measuring electrode unit; and
an analysis device that includes a correction section, wherein:
the correction section corrects a measurement result obtained from the first measurement unit, and
the correction of the measurement result obtained from the first measurement unit is based on a measurement result obtained from the second measurement unit.

16. The electrical measuring system according to claim 15, wherein the electrical measuring apparatus and the analysis device are connected via a network.

17. An electrical measuring method, comprising:
measuring an electrical property of a liquid biological sample based on an electrical measuring cartridge including:
a biological sample holding section that accommodates the liquid biological sample containing a sedimenting component;
a measuring electrode unit that is fixed to the biological sample holding section, wherein:
the measuring electrode unit comprises a first pair of electrodes, and
the first pair of electrodes electrically measures a state of the liquid biological sample; and
a sedimentation measuring electrode unit that is fixed to a position at a height different from a height of the measuring electrode unit of the biological sample holding section, wherein:
the sedimentation measuring electrode unit comprises a second pair of electrodes;
the second pair of electrodes electrically measures a degree of sedimentation of the sedimenting component, and
the measuring electrode unit and the sedimentation measuring electrode unit are fixed as parts of an inner wall of the biological sample holding section.

18. The electrical measuring method according to claim 17, further comprising:
applying a first voltage to the measuring electrode unit;
applying a second voltage to the sedimentation measuring electrode unit;
measuring an electrical property obtained from the measuring electrode unit; and
measuring an electrical property obtained from the sedimentation measuring electrode unit.

* * * * *